United States Patent
Whitaker et al.

[11] Patent Number: 5,645,161
[45] Date of Patent: Jul. 8, 1997

[54] FRAGRANCE PACKET SAMPLER

[75] Inventors: Douglas Whitaker, Chattanooga, Tenn.; Sven Dobler, New York, N.Y.

[73] Assignee: Orlandi Inc.; a part interest

[21] Appl. No.: 589,796

[22] Filed: Jan. 22, 1996

[51] Int. Cl.$^6$ .................................................. F17C 13/00
[52] U.S. Cl. ........................ 206/0.5; 206/581; 206/484; 428/905; 220/359
[58] Field of Search ................... 206/0.5, 484, 581, 206/232, 823; 283/56, 903; 132/320, 317, 333, 79; 428/35.2, 35.4, 35.7, 36.6, 36.7, 905; 239/56; 220/359; 229/125.35

[56] References Cited

U.S. PATENT DOCUMENTS

| | | | |
|---|---|---|---|
| 3,616,898 | 11/1971 | Massie | 206/484 |
| 4,484,768 | 11/1984 | Norfleet | 229/92.8 |
| 4,612,223 | 9/1986 | Spector | 206/0.5 |
| 4,824,707 | 4/1989 | Spector | 428/905 |
| 5,248,537 | 9/1993 | Giannavola | 428/905 |
| 5,419,958 | 5/1995 | Charbonneau | 428/905 |

*Primary Examiner*—Paul T. Sewell
*Assistant Examiner*—Nhan T. Lam

[57] ABSTRACT

A pull-apart fragrance sampler is provided which may be produced in-line and without the use of pressure sensitive materials. The sampler includes a carrier defining a fold line, barrier applied to the carrier and centered with respect to the fold line such that the fold line divides the barrier into a first half and a second half, and a fragrance sample applied to one of the first and second halves of the barrier. The carrier and barrier are folded over upon themselves along the fold line and a seal is formed around the fragrance sample without the use of pressure sensitive materials to bind the two halves of the sampler together. The seal and barrier define a pocket which will substantially prevent the premature release of said fragrance from the sampler. The seal may be a heat seal, an adhesive seal, or a cohesive seal. The barrier may be an aqueous based curable coating, an organic based curable coating, or a film. An ultra-violet curable coating is the preferably coating, and the preferable material for the film is a saran coated polyethylene. If the film is used for barrier, then a heat seal is provided. Conversely, if a coating is provided for the barrier, then the adhesive or cohesive is used to form the seal.

2 Claims, 1 Drawing Sheet

FRAGRANCE PACKET SAMPLER

BACKGROUND OF THE APPLICATION

This invention relates to fragrance samplers provided in magazines and the like.

Pull-apart fragrance samplers ("pull-aparts") are well known and widely used in the fragrance industries. Pull-aparts contain microencapsulated fragrances. When the pull-apart is opened, the microcapsules break, releasing the fragrance for the consumer to sample. Such samplers are provided as magazine and catalog inserts as well as direct mail samplers and statement enclosures for department stores.

There are several manufacturers of pull-aparts serving the fragrance industry. In order to compete with each other, it has been a constant battle to get the fragrance houses' approval for a particular fragrance in pull-apart sampler form. Each manufacturer of pull-aparts submits samples of its particular pull-apart for evaluation. If the rendition of fragrance is comparable between suppliers, many times the approval is awarded to the supplier with the strongest most effusive and overpowering delivery of a fragrance. Realizing this, suppliers of pull-aparts have steadily increased the concentration of fragrance in the pull-apart to the point the odor cannot be properly and completely maintained. Consequently, the pull-aparts smell of fragrance before the sampler is opened. This is what is termed "premature release" of the fragrance.

Modern magazines typically insert three, four, and sometimes as many as five pull-apart samplers into their publications, most of which experience premature release of fragrance. Initially, the fragrance houses whose fragrance was being so promoted liked this, and encouraged this effect. It became necessary to have premature release to compete with competitors who had an insert elsewhere in the magazine. Eventually, the entire magazine would reek of as many as five different fragrances.

As a result, the fragrance houses began to complain that their fragrance was overpowered by the pull-apart on the next pages and that there was no sense in sampling their fragrance because it was contaminated by other fragrances. Threatened by the loss of advertising dollars from the fragrance houses, some the magazine publishers decided to limit the number of pull-apart inserts per issue. This seemed to satisfy the fragrance houses somewhat; now there would be only two other pull-apart inserts with premature release of fragrance with which to compete. This decision caused manufacturers to severely cut production volumes of pull-aparts.

It was not until the postal workers, and more importantly consumers and magazine subscribers, complained that their privacy was being invaded by these unwanted odors, did the problem get serious attention. Consumers claimed that these inserts with premature release of fragrance caused nausea, headaches, rashes and allergic reactions. Many subscribers of magazines have canceled their subscriptions with complaints that they cannot even stand for the magazine to be in their homes. The consumers' complaints caught the attention of the state and federal legislators and the issue was brought before many state governments. New York and California, the biggest markets for fragrances, threatened the industry with laws that would as much as completely outlaw pull-apart samplers.

In an effort to solve the problem of premature release, manufacturers began to develop alternative sampling devises. Products such as SCENT SEAL, available from Scent Seal, Inc. of Los Angleles, Calif., were introduced. This product provides improved containment properties and allows marketers to sample a wet, liquid fragrance formulation. Traditional pull-apart samplers involve fragrance that is applied wet, but is rendered dry due to moisture evaporation. However, it is difficult to produce a pull-apart sampler which samples a wet, liquid fragrance formulation with improved containment properties in an in-line, print production process. SCENT SEAL involves a pressure sensitive label construction. This label is produced separately and is then affixed to a carrier, such as a printed page.

In an effort to resolve these problems and to avoid state and federal regulations restricting the use of pull-aparts, the manufacturers of pull-aparts set up a committee, headed by the CTFA (Cosmetic Toiletries and Fragrance Association) to establish self-regulatory guidelines for the manufacture of pull-aparts without premature release of fragrance. The committee determined that most instances of premature release were due to incidental, microcapsule breakage and leakage. The committee limited the diameter of the microcapsule contained within the pull-apart, the strip length and width, the paper stocks available to print on and many other items that have deteriorated the effectiveness of the pull-apart sampler. Even with these guidelines, the problem persists, and has raised serious questions as to whether or not the manufacturers can be trusted to be self-regulating, and more importantly, whether or not the problem can ever be solved using existing technology.

SUMMARY OF THE INVENTION

One object of the present invention is to provide a fragrance sampler which will substantially contain, eliminate, or absorb prematurely released odors.

Another object is to provide such a sampler which can be produced easily and economically.

Another object is to provide such a sampler which provides containment properties that allow wet, liquid fragrance sampling.

Another object is to provide such a sampler which uses a seal which permits the sampler to be produced in-line.

Another object is to provide such a sampler which does not require pressure sensitive construction.

These and other objects will become apparent to those skilled in the art in light of the following disclosure and accompanying drawings.

In accordance with the invention, generally stated, a pull-apart fragrance sampler is provided which may be produced in-line and without the use of pressure sensitive materials. The sampler includes a carrier, a fold line formed in the carrier; a barrier applied to the carrier and centered with respect to the fold line, the fold line dividing the barrier into a first half and a second half, and a wet fragrance sample applied to one of the first and second halves of the barrier. The carrier and barrier are folded over upon themselves along the fold line and a seal is formed around the fragrance sample without the use of pressure sensitive materials to bind the two halves of the sampler together. The seal and barrier define a pocket which will substantially prevent the premature release of said fragrance from the sampler.

The seal may be a heat seal, an adhesive seal, or a cohesive seal. The barrier may be an aqueous based curable coating, an organic based curable coating, or a film. An ultra-violet curable coating is the preferably coating, and the preferable material for the film is a saran coated polyesther. If the film is used for barrier, then a heat seal is provided.

Conversely, if a coating is provided for the barrier, then the adhesive or cohesive is used to form the seal.

DESCRIPTION OF THE PREFERRED EMBODIMENT

Figure 1:
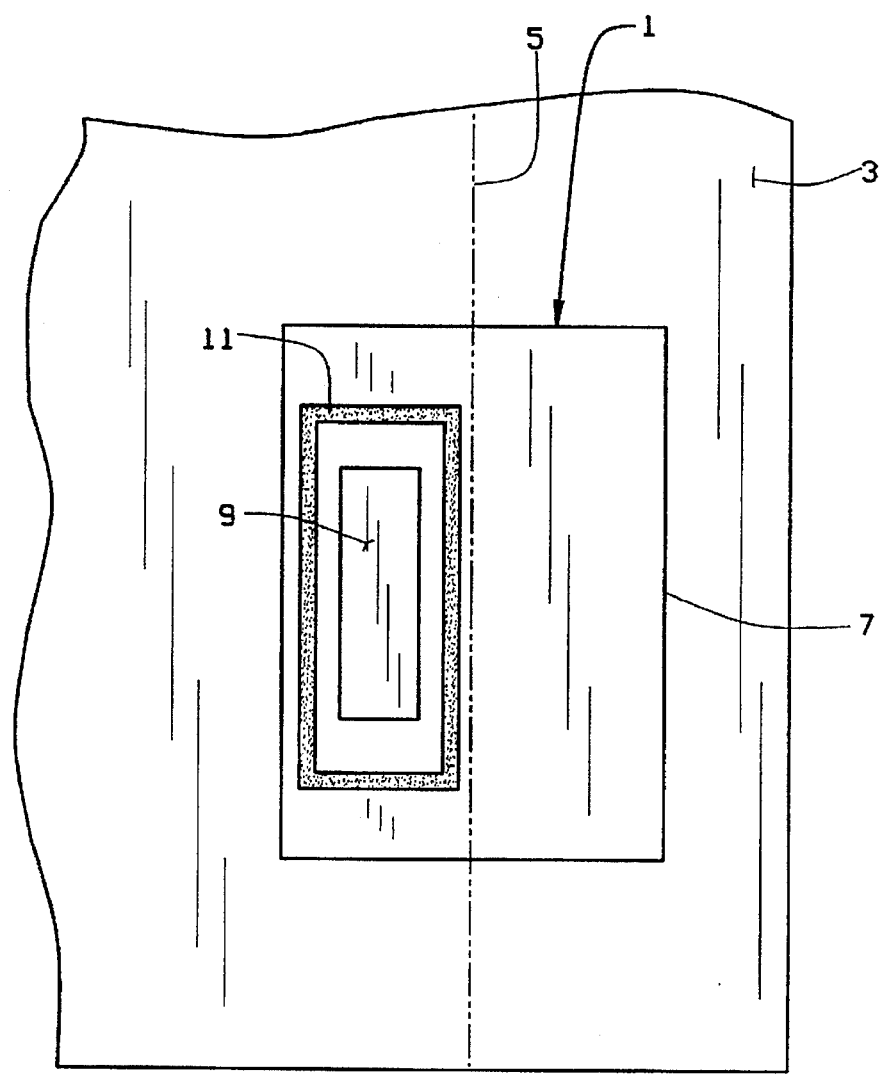
FIG. 1 is a plan view of a fragrance sampler of the present invention prior to placement in a magazine, insert, etc.
Figure 2:
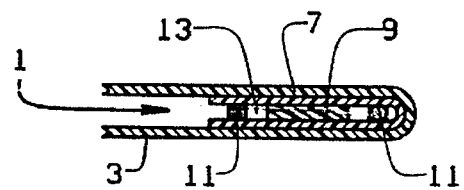
FIG. 2 is an enlarged schematical cross-sectional view of the sampler when folded and sealed.

A fragrance sampler 1 of the present invention is shown in FIG. 1 in an unfolded or opened state positioned on a carrier 3 such as a page of a magazine, an insert in a catalog, etc. The carrier has a fold line 5. The sampler 1 includes a symmetrical barrier 7 which is positioned over and generally centered with respect to the fold line 5 of the carrier. The barrier 7 is may be an aqueous or organic based, heat-settable coating, or a film. The coating, if used, is preferably an ultra-violet curable coating; and the film, if used, is preferably a saran coated polyesther. The fold line 5 divides the barrier 7 into a first half and a second half. A deposit of wet fragrance 9, such as a micro-encapsulated fragrance or a liquid fragrance in a polymer system, is deposited on one of the halves of the barrier 7 and is surrounded by a sealing area 11.

The carrier 3 is typically produced on a web offset or lithographic printing press. After the printing stage (i.e., printing the graphics of the insert), the barrier 7 is deposited on a narrow, defined area of the paper carrier 3. If a coating is used for the barrier 7, then the barrier 7 is cured or set. The fragrance 9 is then deposited on the barrier 7, preferably to be generally centered with respect to one of the halves of the barrier. The barrier 7 and carrier 3 are then folded over to cover the fragrance deposit and a seal is formed around the deposit. The seal 11 is then formed around the fragrance sample 9 to fully encapsulate the fragrance to substantially prevent premature release of the fragrance. If the barrier 7 is a film, the seal 11 may be formed as a heat seal. Alternatively, an adhesive or cohesive may be used which will secure or bond the two halves of the barrier together. If the seal is formed from an adhesive or cohesive which will hold the barrier to itself, the adhesive or cohesive is deposited around the fragrance sample prior to folding of the carrier 3 and barrier 7. The barrier 7 is formed of a material which is impermeable to the fragrance. Thus, the fragrance will not be able to seep through the barrier 7. The seal 11, in combination with the folded barrier 7, defines an area or pocket 13 which will substantially contain the fragrance to prevent the fragrance from escaping the pocket 13.

Because the seal is a heat seal or formed from an adhesive or cohesive agent, the wet fragrance sampler may be formed without the need of pressure sensitive seals, as is presently common. This allows in-line production of the sampler 1 to be more economical.

The deposit of the barrier 7, fragrance 9, as well as the folding, sealing, and die cutting of samples into individual samples may be performed in line, directly on the printed page.

As variations within the scope of the appended claims may be apparent to those skilled in the art, the foregoing description is set forth only for illustrative purposes and is not meant to be limiting.

We claim:

1. A pull-apart film laminated fragrance sampler including a carrier, a fold line formed in said carrier, a barrier applied to the carrier to cover the fold line, said barrier comprising film of saran coated polyester; the fold line dividing the barrier into a first portion and a second portion; a liquid fragrance sample applied to one of said first and second portions of said barrier; wherein said carrier and barrier are folded over upon themselves along said fold line to define a pocket in which said fragrance sample is situated, said first and second portions of said barrier being heat sealed around said fragrance sample to hold said first and second portions of said barrier together and to substantially prevent the premature release of said fragrance from said sampler.

2. The pull-apart fragrance sampler of claim 1 wherein said barrier further comprises a coating, and wherein said coating includes an ultra-violet curable coating.

* * * * *